United States Patent [19]

Itho et al.

[11] Patent Number: 4,478,838
[45] Date of Patent: Oct. 23, 1984

[54] 1-(3,4,5-TRIMETHOXYCINNAMOYL)-4-ALKYLAMINOCARBONYLETHYL PIPERAZINES

[75] Inventors: Yasuo Itho; Hideo Kato; Eiichi Koshinaka; Nobuo Ogawa; Sakae Kurata; Kagari Yamagishi, all of Fukui, Japan

[73] Assignee: Hokuriku Pharmaceutical Co., Ltd., Katsuyamashi, Japan

[21] Appl. No.: 441,635

[22] Filed: Nov. 15, 1982

[30] Foreign Application Priority Data

Nov. 19, 1981 [JP] Japan .................. 56-184478

[51] Int. Cl.³ .................. A61K 31/495; C07D 241/04
[52] U.S. Cl. ........................... 424/250; 544/386
[58] Field of Search ............... 542/440, 429; 424/250

[56] References Cited

U.S. PATENT DOCUMENTS

| 3,634,411 | 1/1972 | Fauran et al. | 542/440 |
| 4,016,154 | 4/1977 | Turin et al. | 542/440 |
| 4,029,650 | 6/1977 | Raynaud et al. | 542/440 |
| 4,178,442 | 12/1979 | Bourgery et al. | 542/440 |
| 4,368,199 | 1/1983 | Ancher et al. | 542/440 |

FOREIGN PATENT DOCUMENTS 556791 5/1957 Belgium .................. 542/440

Primary Examiner—Glennon H. Hollrah
Assistant Examiner—James H. Turnipseed
Attorney, Agent, or Firm—Gordon W. Hueschen

[57] ABSTRACT 1-(3,4,5-Trimethoxycinnamoyl)-4-aminocarbonylethyl-substituted piperazine derivatives represented by general formula (I):

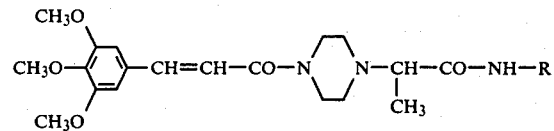

wherein R is a straight- or branched-chain alkyl group having 1 to 6 carbon atoms or a cycloalkyl group having 5 to 7 carbon atoms, and pharmaceutically acceptable acid addition salts thereof are disclosed.

The 1-(3,4,5-trimethoxycinnamoyl)-4-aminocarbonylethyl-substituted piperazine derivatives are useful as vasodilator agents.

5 Claims, No Drawings

1-(3,4,5-TRIMETHOXYCINNAMOYL)-4-ALKYLAMINOCARBONYLETHYL PIPERAZINES

BACKGROUND OF THE INVENTION

1. Field of the Invention

The present invention relates to novel 1-(3,4,5-trimethoxycinnamoyl)-4-aminocarbonylethyl-substituted piperazine derivatives and pharmaceutically acceptable acid addition salts thereof which exhibit an effective vasodilatory activity, and to a process for the preparation thereof, pharmaceutical compositions thereof, and method of treating therewith.

Particularly, this invention relates to novel 1-(3,4,5-trimethoxycinnamoyl)-4-aminocarbonylethyl-substituted piperazine derivatives represented by general formula (I):

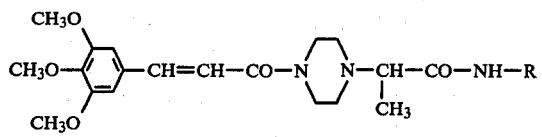

wherein R is a straight- or branched-chain alkyl group having 1 to 6 carbon atoms or a cycloalkyl group having 5 to 7 carbon atoms, and pharmaceutically acceptable acid addition salts thereof, a process for the preparation thereof, pharmaceutical compositions thereof, and method of treating therewith.

2. Description of the Prior Art

Many vasodilators have been already researched and developed, but there are still problems which should be improved with regard to drug effects and side effects.

For example cinepazide (general name, Merck Index, 9th Edition, 2282), represented by formula (II):

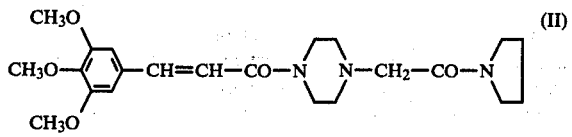

is well known as a vasodilator and has been widely provided for clinical use.

However, cinepazide suffers from the defect that, while the toxicity is low, the drug effect is weak.

For purposes of improving the vasodilatory action of cinepazide represented by formula (II), cinpropazide (general name, USAN and the USP Dictionary of Drug Names, 1982, page 109) represented by formula (III):

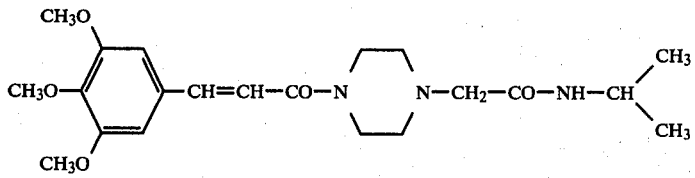

has been prepared. It was found that the toxicity became greater while the drug effect became stronger. Therefore, it was difficult to provide for clinical use.

SUMMARY OF THE INVENTION

As a result of extensive investigations, it has been found that novel 1-(3,4,5-trimethoxycinnamoyl)-4-aminocarbonyl-substituted piperazine derivatives represented by formula (I) and their pharmaceutically acceptable acid addition salts have a low toxicity and possess an effective vasodilatory activity, so that they can be used as a medicine with extremely favorable results.

DETAILED DESCRIPTION OF THE INVENTION

In the foregoing formula (I), methyl, ethyl, propyl, isopropyl, butyl, isobutyl, sec-butyl, tert-butyl, pentyl, hexyl, cyclopentyl, cyclohexyl, and cycloheptyl groups, and the like, are encompassed by the symbol R.

The compounds represented by general formula (I) can be converted into the corresponding pharmaceutically-acceptable acid addition salts in a conventional manner and the base can be liberated from the so prepared acid addition salts if necessary.

Examples of the pharmaceutically-acceptable acid addition salts of the compounds represented by general formula (I), are salts of mineral acids such as hydrochloric acid, nitric acid, sulfuric acid, hydrobromic acid, hydroiodic acid, phosphoric acid and the like, and organic acids such as acetic acid, maleic acid, fumaric acid, citric acid, oxalic acid, tartaric acid and the like, maleic acid and fumaric acid being especially preferred as acid addition salts.

According to the present invention, the novel 1-(3,4,5-trimethoxycinnamoyl)-4-aminocarbonylethyl-substituted piperazine derivatives represented by general formula (I) can be prepared by reacting 1-aminocarbonylethyl-substituted piperazine derivatives represented by general formula (IV):

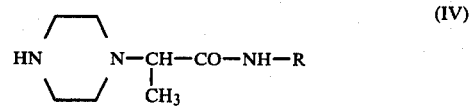

wherein R is as defined above, with a 3,4,5-trimethoxycinnamoyl halogenide represented by general formula (V):

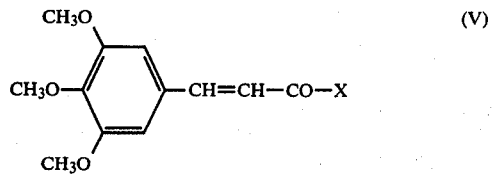

wherein X is a halogen atom, especially a chlorine or bromine atom.

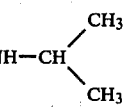

According to a particularly preferred embodiment of the process of this invention, 1 part of a 1-aminocarbonylethyl-substituted piperazine derivative represented by general formula (IV) is reacted with at least 1 part, preferably 1.2 to 1.3 parts, of 3,4,5-trimethoxycinnamoyl halogenide represented by general formula (V) in the presence of at least 1 part, preferably 1.2 to 1.3 parts, of base as acid-accepting agent in anhydrous inert organic solvent.

As inert organic solvent used in the process of this invention, any solvent can be used unless the solvent inhibits the reaction. Typical examples of suitable solvents are acetone, ether, tetrahydrofuran, dioxane, benzene, toluene, chloroform and the like.

As bases acting as acid-accepting agent in the process of this invention, may be mentioned, for example, triethylamine, pyridine, potassium carbonate and the like.

The reaction can be carried out at a temperature between room temperature and the boiling point of the organic solvent used, preferably at or about room temperature.

The 1-aminocarbonylethyl-substituted piperazine derivatives represented by general formula (IV), which can be used as the starting materials for the process of this invention, are all new and novel and the preparation thereof is described in the following.

The 3,4,5-trimethoxycinnamoyl halogenide represented by general formula (V) can be prepared by conversion of 3,4,5-trimethoxycinnamic acid into an acid halogenide according to a conventional method, preferably at the time of using. According to another embodiment of the process for preparing the compounds in accordance with this invention, the compound of formula (I) can be prepared by reacting 1-(3,4,5-trimethoxycinnamoyl)piperazine, represented by formula (VI):

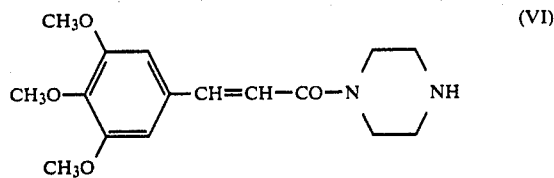

with an aminocarbonylethyl halide represented by general formula (VII):

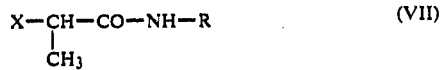

wherein group R is as defined above and X is a halogen atom, especially a chlorine or bromine atom, in the presence of a base as acid-accepting agent.

According to a particularly preferred embodiment of the process of this invention, 1 part of 1-(3,4,5-trimethoxycinnamoyl)piperazine represented by general formula (VI) is reacted with at least 1 part, preferably 1.2 to 1.3 parts, of aminocarbonylethyl halide represented by general formula (VII) in the presence of at least 1 part, preferably 1.2 to 1.3 parts, of a base as acid accepting agent in anhydrous inert organic solvent.

As inert organic solvent used in the process of this invention, any solvent can be used unless the solvent inhibits the reaction, for example, acetone, ethanol, ether, tetrahydrofuran, dioxane, benzene, toluene, chloroform and the like.

Representative bases acting as acid-binding agent which may be used in the process of this invention are, for example, triethylamine, pyridine, potassium carbonate and the like. Also, the reaction is generally carried out at a temperature between room temperature and the boiling point of the organic solvent used, preferably at the boiling point of the organic solvent employed.

The 1-(3,4,5-trimethoxycinnamoyl)piperazine represented by general formula (VI) as a starting material is known and is described in, e.g., Japanese Patent Application (OPI) 10282/77.

Also, aimost of the aminocarbonylethyl halides represented by general formula (VII) are known and described in, e.g., Journal of the American Chemical Society, 78, 6123 (1956), and are prepared by reacting 2-chloropropionyl chloride with the amine. Any new compounds are easily prepared in the conventional manner.

A compound of the present invention represented by general formula (I) can be administered per os, e.g., in the form of pills or tablets, in which it may be present together with the usual pharmaceutical carriers, conventionally by compounding the compounds of this invention together with a customary carrier or adjuvant, such as talc, magnesium stearate, starch, lactose, gelatin, any of numerous gums, and the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, terra alba, dicalcium acacia, or the like. Representative liquid carriers are peanut oil, sesame oil, olive oil, water, or the like. The active agents of this invention can be conveniently administered in such compositions containing active ingredient so as to eventually be within the dosage range illustrated hereafter. Thus, a wide variety of pharmaceutical forms suitable for many modes of administration and dosages may be employed. For oral administration, the active ingredient and pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion, whereas, for parenteral administration, the composition may be in the form of a sterile solution.

The method of using the compounds of this invention comprises internally or externally administering a compound of this invention, preferably orally or parenterally and preferably admixed with the pharmaceutical carrier, for example, in the form of any of the above compositions, or filled into a capsule, to alleviate conditions to be treated and symptoms thereof in a living animal body. Illustratively, it may be used in an amount of about 10 to about 300 mg. per unit dose, preferably 100 to 200 mg. for an oral dose, while parenteral dosages are usually less and ordinarily about one-half of the oral dose. The unit dose is preferably given a suitable number of times daily, typically three times. The daily dose may vary depending upon the number of times given. Naturally, a suitable clinical dose must be adjusted in accordance with the condition, age, and weight of the patient, and it goes without saying that the enhanced activities of the compounds of the invention, together with their reduced side effects, also make them suitable for wide variations, and this invention therefore should not be limited by the exact ranges stated. The exact dosage, both unit dosage and daily dosage, will of course have to be determined according to established medical principles.

The thus-prepared 1-(3,4,5-trimethoxycinnamoyl)-4-aminocarbonylethyl-substituted piperazine derivatives represented by general formula (I) and pharmaceutically acceptable acid addition salts thereof exhibit an effective vasodilatory activity and can be used as a medicine extremely favorably. The potentiating effect of the adenosine action is shown in Table 1 as one example representing the effective vasodilatory activity of the present compounds.

As reference drugs, the drugs represented by formula (II) and (III), which possess a structure similar to that of the present compounds, are used.

It is known that adenosine is a substance possessing a vasodilatory activity within a body (American Journal of Physiology, 204, 317(1963)), and the present compounds possess a powerful potentiating effect on the adenosine vasodilatory action.

This potentiating effect of the present compounds is extremely strong, 4 to 7 times stronger than that of cinepazide represented by formula (II), and 2 to 4 times stronger than that of cinpropazide represented by formula (III).

TEST COMPOUNDS

Compound of Invention 1 (Example 3)

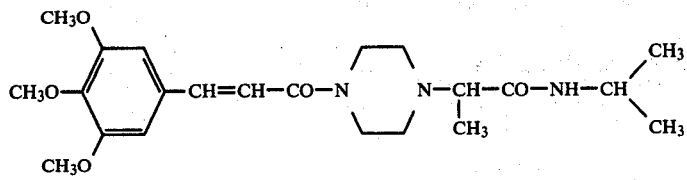

Compound of Invention 2 (Example 10)

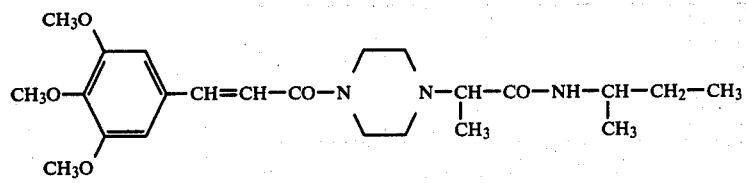

Compound of Invention 3 (Example 6)

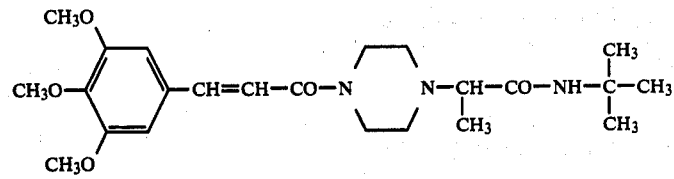

Compound of Invention 4 (Example 7)

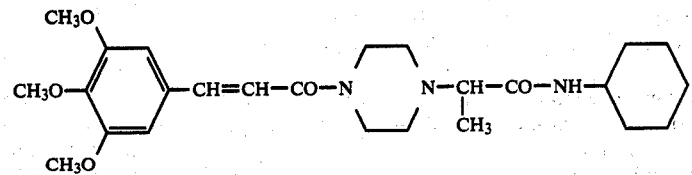

Reference Drug 1 (Cinepazide)

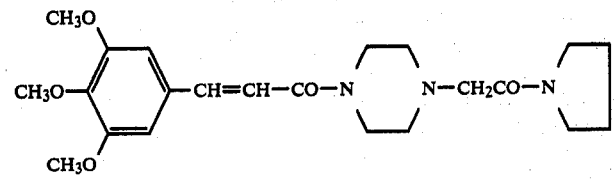

Reference Drug 2 (Cinepropazide)

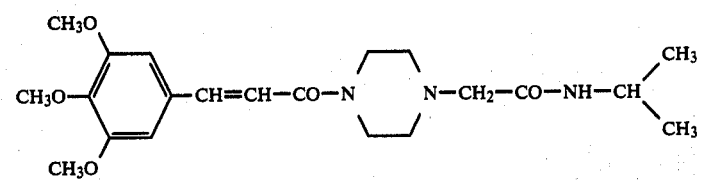

EXPERIMENT

According to the method of Ishida et al. (British Journal of Pharmacology, 68, 343 (1980)), the heart of a male guinea-pig weighing 300 to 400 g is isolated and set in the organ bath.

The end of the heart is connected with a transducer and resulting tension is recorded with equivalent scales. Adenosine is added cumulatively as $1\times10^{-8}$, $3\times10^{-8}$, $1\times10^{-7}$, $3\times10^{-7}$, $1\times10^{-6}$, $1\times10^{-5}$, $3\times10^{-5}$ g/ml and the dose-response curve with respecting with depression of heart contraction by adenosine is obtained.

The dose-response curve of adenosine in the presence of $1\times10^{-6}$ g/ml of test compound is likewise obtained.

The potentiating effect of the test compounds is shown as the value (A) represented as follows:

$$(A) = \frac{\text{Concentration of adenosine at 50\% contractive action}}{\text{Concentration of adenosine in the presence of test compound at 50\% contractive action}}$$

TABLE 1

| The potentiating effect of the adenosine action | | |
|---|---|---|
| Test Compounds | Adenosine Potentiating Effect | Potency Ratio* |
| Compound 1 | 12.9 | 4.3 |
| Compound 2 | 20.3 | 6.8 |
| Compound 3 | 11.8 | 3.9 |
| Compound 4 | 10.4 | 3.5 |
| Reference 1 | 3.0 | 1.0 |
| Reference 2 | 4.8 | 1.6 |

*the effect of Reference 1 is defined as 1.0

The following examples are given by way of illustration only and are not to be construed as limitations of this invention, many variations of which are possible without departing from the scope and spirit thereof.

EXAMPLE 1

(a) 1-(3,4,5-Trimethoxycinnamoyl)-4-[1-(ethylaminocarbonyl)ethyl]piperazine 17.19 g of 3,4,5-trimethoxycinnamoyl chloride and 6.78 g of triethylamine are added with ice cooling to a solution of 9.54 g of 1-[1-(ethylaminocarbonyl)ethyl]piperazine in 200 ml of chloroform, and the resulting solution is kept standing at room temperature for 1 hour.

The solvent is distilled off and a mixture of benzene and aqueous hydrochloric acid solution is added to the residue and shaken.

The insoluble substances are removed by filtration and the aqueous layer is separated.

The aqueous layer is made alkaline with potassium carbonate and extracted with chloroform.

The chloroform layer is washed with water and dehydrated.

The solvent is distilled off and 17.00 g of yellowish-brown crystals are obtained.

Recrystallization from ethyl acetate gives colorless scales, m.p. 168°-169° C.

IR Spectrum $\nu$(KBr)cm$^{-1}$:

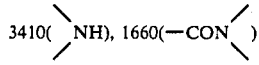

Elementary analysis: $C_{21}H_{31}N_3O_5$: Calculated: C, 62.20; H, 7.71; N, 10.36. Found: C, 62.02; H, 7.80; N, 10.48.

(b) 1-[1-(Ethylaminocarbonyl)ethyl]piperazine is prepared as follows:

7.96 g of potassium carbonate and a solution of 7.80 g of N-ethyl-2-chloropropionamide in 50 ml of ethanol are added to a solution of 9.92 g of piperazine in 100 ml of ethanol, and the resulting solution is refluxed for 16 hours.

After reaction is complete, the insoluble substances are removed by filtration and the solvent is distilled off. The residue is acidified with aqueous hydrochloric acid solution and washed with chloroform. The resulting solution is made alkaline with potassium carbonate and washed with chloroform again.

The aqueous layer is saturated with potassium carbonate and extracted with chloroform.

The chloroform layer is dehydrated.

The solvent is distilled off and 9.04 g of pale yellow liquid are obtained.

IR Spectrum $\nu$(film)cm$^{-1}$:

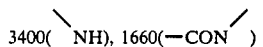

EXAMPLE 2

(a) 1-(3,4,5-Trimethoxycinnamoyl)-4-[1-(propylaminocarbonyl)ethyl]piperazine 20.00 g of 3,4,5-trimethoxycinnamoyl chloride and 11.77 ml of triethylamine are added with ice cooling to a solution of 12.90 g of 1-[1-(propylaminocarbonyl)ethyl]piperazine in 200 ml of chloroform and stirred at room temperature for one-half an hour.

After reacting, the solvent is distilled off and a mixture of ethyl acetate and aqueous hydrochloric acid solution is added to the residue and shaken.

The insoluble substances are removed by filtration and the aqueous layer is separated.

The aqueous layer is made alkaline with potassium carbonate and extracted with chloroform.

The chloroform layer is washed with water and dehydrated.

The solvent is distilled off and 22.50 g of yellowish-brown crystals are obtained.

Recrystallization from ethyl acetate gives colorless scales, m.p. 172°-173° C.

IR Spectrum $\nu$(KBr)cm$^{-1}$:

Elementary analysis: $C_{22}H_{33}N_3O_5$: Calculated: C, 62.99; H, 7.93; N, 10.02. Found: C, 62.93; H, 8.08; N, 9.88.

(b) 1-[1-(Propylaminocarbonyl)ethyl]piperazine is prepared as follows:

14.53 g of potassium carbonate and a solution of 20.40 g of N-propyl-2-bromopropionamide in 100 ml of ethanol are added to a solution of 18.11 g of piperazine in 200 ml of ethanol, and the resulting solution is refluxed for 2 hours. After reaction is complete, the insoluble substances are removed by filtration and the solvent is distilled off. The residue is acidified with aqueous hydrochloric acid solution and washed with chloroform. The resulting solution is made alkaline with potassium carbonate and washed with ethyl acetate.

The aqueous layer is saturated with potassium carbonate and extracted with chloroform, and the chloroform layer is dehydrated.

The solvent is distilled off and 16.50 g of yellow liquid are obtained.

IR Spectrum $\nu$(film)cm$^{-1}$:

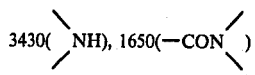

EXAMPLE 3

(a) 1-(3,4,5-Trimethoxycinnamoyl)-4-[1-(isopropylaminocarbonyl)ethyl]piperazine 15.15 g of 3,4,5-trimethoxycinnamoyl chloride and 8.92 ml of triethylamine are added with ice cooling and stirring to a solution of 9.80 g of 1-[1-(isopropylaminocarbonyl)ethyl]piperazine in 200 ml of chloroform, and the resulting solution is stirred at room temperature for 1 hour.

Thereafter, the procedure according to Example 2 (a) is repeated and 18.60 g of brown crystals are obtained. Recrystallization from ethyl acetate gives colorless scales, m.p. 188°–189° C.

IR Spectrum $\nu$(KBr)cm$^{-1}$:

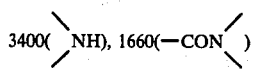

Elementary analysis: $C_{22}H_{33}N_3O_5$: Calculated: C, 62.99; H, 7.93; N, 10.02. Found: C, 62.65; H, 8.02; N, 9.89.

(b) 1-[1-(Isopropylaminocarbonyl)ethyl]piperazine is prepared as follows:

9.70 g of potassium carbonate and a solution of 10.50 g of N-isopropyl-2-chloropropionamide in 70 ml of ethanol are added to a solution of 12.09 g of piperazine in 100 ml of ethanol, and the resulting solution is refluxed for 14 hours.

Thereafter, the procedure according to Example 2 (b) is repeated and 9.80 g of pale yellow liquid are obtained.

IR Spectrum $\nu$(film)cm$^{-1}$:

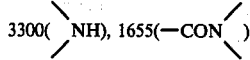

EXAMPLE 4

1-(3,4,5-Trimethoxycinnamoyl)-4-[1-(isopropylaminocarbonyl)ethyl]piperazine 0.18 of potassium carbonate and a solution of 0.33 g of N-isopropyl-2-bromopropionamide in 5 ml of ethanol are added to a solution of 0.40 g of 1-(3,4,5-trimethoxycinnamoyl)piperazine in 5 ml of ethanol and the resulting solution is refluxed for 15 hours.

Thereafter, the procedure according to Example 2 (a) is repeated and 0.22 g of pale yellow crystals are obtained. Recrystallization from ethyl acetate gives colorless scales, m.p. 188°–189° C.

This product is identical with the product obtained in Example 3 (a) in IR spectrum and the NMR spectrum.

EXAMPLE 5

(a) 1-(3,4,5-Trimethoxycinnamoyl)-4-[1-(isobutylaminocarbonyl)ethyl]piperazine 14.40 g of 3,4,5-trimethoxycinnamoyl chloride is added to a solution of 9.20 g of 1-[1-(isobutylaminocarbonyl)ethyl]piperazine and 5.70 g of triethylamine in 200 ml of chloroform, and the resulting solution is kept standing at room temperature for 1 hour.

Thereafter, the procedure according to Example 2 (a) is repeated and 15.56 g of yellowish-brown liquid are obtained. Recrystallization from ethyl acetate gives colorless scales, m.p. 171°–173° C.

IR Spectrum $\nu$(KBr)cm$^{-1}$:

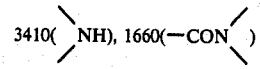

Elementary analysis: $C_{23}H_{35}N_3O_5$: Calculated: C, 63.72; H, 8.14; N, 9.69. Found: C, 63.47; H, 8.24; N, 9.49.

(b) 1-[1-(Isobutylaminocarbonyl)ethyl]piperazine is prepared as follows:

1.38 g of potassium carbonate and a solution of 1.63 g of N-isobutyl-2-chloropropionamide in 10 ml of ethanol are added to a solution of 1.72 g of piperazine in 15 ml of ethanol, and the resulting solution is refluxed for 23 hours.

Thereafter, the procedure according to Example 2 (b) is repeated and 1.86 g of yellow liquid are obtained.

IR Spectrum $\nu$(film)cm$^{-1}$:

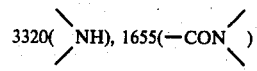

EXAMPLE 6

(a) 1-(3,4,5-Trimethoxycinnamoyl)-4-[1-(tert-butylaminocarbonyl)ethyl]piperazine 0.78 g of 3,4,5-trimethoxycinnamoyl chloride is added to a solution of 0.50 g of 1-[1-(tert-butylaminocarbonyl)ethyl]piperazine and 0.31 g of triethylamine in 15 ml of chloroform, and the resulting solution is stirred at room temperature for 1 hour.

Thereafter, the procedure according to Example 1 (a) is repeated and 0.93 g of yellowish-brown crystals are obtained.

Recrystallization from ethanol gives colorless scales, m.p. 202°–203° C.

IR Spectrum $\nu$(KBr)cm$^{-1}$:

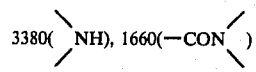

Elementary analysis: $C_{23}H_{35}N_3O_5$: Calculated: C, 63.72; H, 8.14; N, 9.69. Found: C, 63.65; H, 8.22; N, 9.55.

(b) 1-[1-(tert-Butylaminocarbonyl)ethyl]piperazine is prepared as follows:

10.40 g of potassium carbonate and a solution of 12.26 g of N-(tert-butyl)-2-chloropropionamide in 50 ml of ethanol are added to a solution of 12.90 g of piperazine in 100 ml of ethanol, and the resulting solution is refluxed for 14.5 hours.

Thereafter, the procedure according to Example 2 (b) is repeated and 11.45 g of colorless liquid are obtained.

IR Spectrum $\nu$(film)cm$^{-1}$:

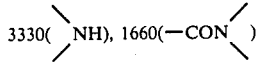
3330( ⟩NH), 1660(—CON⟨ )

EXAMPLE 7

(a) 1-(3,4,5-Trimethoxycinnamoyl)-4-[1-(cyclohexylaminocarbonyl)ethyl]piperazine 0.64 g of 3,4,5-trimethoxycinnamoyl chloride is added to a solution of 0.50 g of 1-[1-(cyclohexylaminocarbonyl)ethyl]piperazine and 0.27 g of triethylamine in 15 ml of chloroform, and the resulting solution is kept standing at room temperature for 20 minutes.

Thereafter, the procedure according to Example 1 (a) is repeated and 0.79 g of yellowish-brown crystals are obtained.

Recrystallization from ethyl acetate gives colorless scales, m.p. 163°–165° C.

IR Spectrum $\nu$(KBr)cm$^{-1}$:

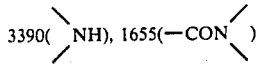
3390( ⟩NH), 1655(—CON⟨ )

Elementary analysis: $C_{25}H_{37}N_3O_5$: Calculated: C, 65.34; H, 8.11; N, 9.14. Found: C, 65.39; H, 8.19; N, 9.19.

(b) 1-[1-(Cyclohexylaminocarbonyl)ethyl]piperazine is prepared as follows:

10.52 g of potassium carbonate and a solution of 17.59 g of N-cyclohexyl-2-bromopropionamide in 70 ml of ethanol are added to a solution of 12.94 g of piperazine in 100 ml of ethanol, and the resulting solution is refluxed for 3 hours.

Thereafter, the procedure according to Example 2 (b) is repeated and 13.96 g of pale yellow liquid are obtained.

IR Spectrum $\nu$(film)cm$^{-1}$:

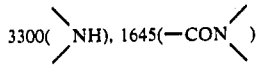
3300( ⟩NH), 1645(—CON⟨ )

EXAMPLE 8

(a) 1-(3,4,5-Trimethoxycinnamoyl)-4-[1-(methylaminocarbonyl)ethyl]piperazine 5.40 g of 3,4,5-trimethoxycinnamoyl chloride is added with stirring at room temperature to a solution of 3.00 g of 1-(1-methylaminocarbonyl)ethyl piperazine in 40 ml of chloroform, and the resulting solution is stirred at room temperature for 30 minutes.

Thereafter, the procedure according to Example 1 (a) is repeated and 3.37 g of colorless crystals are obtained. Recrystallization from ethyl acetate gives colorless crystals, m.p. 172°–175° C.

IR Spectrum $\nu$(KBr)cm$^{-1}$:

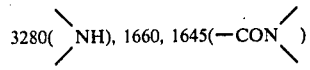
3280( ⟩NH), 1660, 1645(—CON⟨ )

Elementary analysis: $C_{20}H_{29}N_3O_5$: Calculated: C, 61.36; H, 7.47; N, 10.73. Found: C, 61.19; H, 7.16; N, 10.63.

(b) 1-[1-(Methylaminocarbonyl)ethyl]piperazine is prepared as follows:

4.00 g of potassium carbonate and a solution of 3.50 g of N-methyl-2-chloropropionamide in 20 ml of ethanol are added to a solution of 5.00 g of piperazine in 40 ml of ethanol and the resulting solution is refluxed for 13.5 hours.

Thereafter, the procedure according to Example 1 (b) is repeated and 3.44 g of pale yellow liquid are obtained.

IR Spectrum $\nu$(film)cm$^{-1}$:

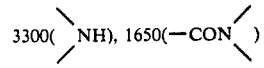
3300( ⟩NH), 1650(—CON⟨ )

EXAMPLE 9

(a) 1-(3,4,5-Trimethoxycinnamoyl)-4-[1-(butylaminocarbonyl)ethyl]piperazine 7.23 g of 3,4,5-trimethoxycinnamoyl chloride is added with stirring at room temperature to a solution of 5.00 g of 1-[1-(butylaminocarbonyl)ethyl]piperazine in 80 ml of chloroform, and the resulting solution is stirred at room temperature for 15 minutes.

Thereafter, the procedure according to Example 1 (a) is repeated and 7.22 g of pale yellow crystals are obtained. Recrystallization from ethyl acetate gives pale yellow plates, m.p. 143.5°–144.5° C.

IR Spectrum $\nu$(KBr)cm$^{-1}$:

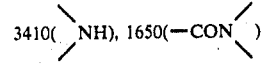
3410( ⟩NH), 1650(—CON⟨ )

Elementary analysis: $C_{23}H_{35}N_3O_5$: Calculated: C, 63.72; H, 8.14; N, 9.69. Found: C, 63.73; H, 8.15; N, 9.54.

(b) 1-[1-(Butylaminocarbonyl)ethyl]piperazine is prepared as follows:

19.40 g of potassium carbonate and a solution of 23.00 g of N-butyl-2-chloropropionamide in 200 ml of ethanol are added to 12.10 g of piperazine, and the resulting solution is refluxed for 19.5 hours.

After reaction is complete, the insoluble substances are removed by filtration and the solvent is distilled off. The residue is acidified with aqueous hydrochloric acid solution and washed with chloroform. The resulting solution is made alkaline with potassium carbonate and washed with ether.

The aqueous layer is saturated with potassium carbonate and extracted with chloroform.

The chloroform layer is dehydrated.

The solvent is distilled off and 12.00 g of yellow liquid are obtained.

IR Spectrum $\nu$(film)cm$^{-1}$:

3300(>NH), 1660(—CON<)

EXAMPLE 10

(a) 1-(3,4,5-Trimethoxycinnamoyl)-4-[1-(sec-butylaminocarbonyl)ethyl]piperazine 6.80 g of 3,4,5-trimethoxycinnamoyl chloride is added with stirring at room temperature to a solution of 4.70 g of 1-1-(sec-butylaminocarbonyl)ethyl piperazine in 50 ml of chloroform, and the resulting solution is stirred at room temperature for 30 minutes.

Thereafter, the procedure according to Example 1 (a) is repeated and 6.80 g of pale yellow crystals are obtained. Recrystallization from ethyl acetate gives pale yellow scales, m.p. 165°–171° C.

IR Spectrum $\nu$(KBr)cm$^{-1}$:

3260(>NH), 1640(—CON<)

Elementary analysis: $C_{23}H_{35}N_3O_5$: Calculated: C, 63.72; H, 8.14; N, 9.69. Found: C, 63.62; H, 8.34; N, 9.86.

(b) 1-[1-(sec-Butylaminocarbonyl)ethyl]piperazine is prepared as follows:

3.80 g of potassium carbonate and a solution of 4.50 g of N-(sec-butyl)-2-chloropropionamide in 20 ml of ethanol are added to a solution of 4.80 g of piperazine in 40 ml of ethanol, and the resulting solution is refluxed for 18 hours.

Thereafter, the procedure according to Example 9 (b) is repeated and 4.85 g of colorless liquid are obtained.

IR Spectrum $\nu$(film)cm$^{-1}$:

3320(>NH), 1660(—CON<)

EXAMPLE 11

(a) 1-(3,4,5-Trimethoxycinnamoyl)-4-[1-(pentylaminocarbonyl)ethyl]piperazine 5.62 g of 3,4,5-trimethoxycinnamoyl chloride is added with stirring at room temperature to a solution of 4.15 g of 1-[1-(pentylaminocarbonyl)ethyl]piperazine in 60 ml of chloroform, and the resulting solution is stirred at room temperature for 20 minutes.

The solvent is distilled off and a mixture of ethyl acetate and aqueous hydrochloric acid solution is added to the residue and shaken.

The precipitates are collected by filtration and added to a mixture of aqueous solution of potassium carbonate and chloroform, and the resulting solution is shaken.

The chloroform layer is separated and washed with water and dehydrated.

The solvent is distilled off and 6.70 g of pale yellow crystals are obtained.

Recrystallization from ethyl acetate gives pale yellow plates, m.p. 138°–139° C.

IR Spectrum $\nu$(KBr)cm$^{-1}$:

3350(>NH), 1655(—CON<)

Elementary analysis: $C_{24}H_{37}N_3O_5$: Calculated: C, 64.41; H, 8.33; N, 9.39. Found: C, 64.41; H, 8.55; N, 9.21.

(b) 1-[1-(Pentylaminocarbonyl)ethyl]piperazine is prepared as follows:

3.89 g of potassium carbonate and a solution of 5.00 g of N-pentyl-2-chloropropionamide in 50 ml of ethanol are added to a solution of 4.85 g of piperazine in 50 ml of ethanol, and the resulting solution is refluxed for 15 hours.

Thereafter, the procedure according to Example 9 (b) is repeated and 4.35 g of pale yellow liquid are obtained.

IR Spectrum $\nu$(film)cm$^{-1}$:

3310(>NH), 1655(—CON<)

EXAMPLE 12

(a) 1-(3,4,5-Trimethoxycinnamoyl)-4-[1-(hexylaminocarbonyl)ethyl]piperazine 6.39 g of 3,4,5-trimethoxycinnamoyl chloride is added with stirring at room temperature to a solution of 5.00 g of 1-[1-(hexylaminocarbonyl)ethyl]piperazine in 80 ml of chloroform, and the resulting solution is stirred at room temperature for 15 minutes.

After reaction is complete, the solvent is distilled off and a mixture of benzene and aqueous hydrochloric acid solution is added to the residue and shaken. The precipitates are collected by filtration and the aqueous layer of the filtrate is separated.

The aqueous layer is made alkaline with potassium carbonate and extracted with chloroform.

The above precipitates are added to a mixture of an aqueous solution of potassium carbonate and chloroform and shaken. The chloroform layer is separated and combined with the above-extracted solution of chloroform, washed with water, and dehydrated.

The solvent is distilled off and 7.27 g of pale yellow crystals are obtained.

Recrystallization from ethanol gives pale yellow prisms, m.p. 119°–122° C.

IR Spectrum $\nu$(KBr)cm$^{-1}$:

3300(>NH), 1645, 1655(—CON<)

Elementary analysis: $C_{25}H_{39}N_3O_5$: Calculated: C, 65.05; H, 8.52; N, 9.10. Found: C, 64.82; H, 8.57; N, 9.26.

(b) 1-[1-(Hexylaminocarbonyl)ethyl]piperazine is prepared as follows:

9.50 g of potassium carbonate and 11.90 g of piperazine are added to a solution of 13.20 g of N-hexyl-2-chloropropionamide in 150 ml of ethanol, and the resulting solution is refluxed for 19 hours.

After reaction is complete, the insoluble substances are removed by filteration and the solvent is distilled off.

The residue is acidified with aqueous hydrochloric acid solution and washed with chloroform. The resulting solution is made alkaline with potassium carbonate and extracted with chloroform.

The chloroform layer is dehydrated.

The solvent is distilled off and distillation under nitrogen atmosphere gives 8.03 g of colorless liquid, b.p. 144°–146° C. (4 mmHg).

IR Spectrum $\nu$(film)cm$^{-1}$:

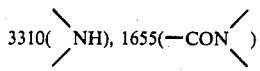

EXAMPLE 13

Other cycloalkyl derivatives.

In the same manner as given in Example 7, the corresponding cyclopentyl, and cycloheptyl compounds are prepared by substituting the appropriate 1-[1-(cycloalkylaminocarbonyl)ethyl]-piperazine for the 1-[1-(cyclohexylaminocarbonyl)ethyl]-piperazine of Example 7, the precise compounds being prepared in this manner being as follows:

1-(3,4,5-Trimethoxycinnamoyl)-4-[1-(cyclopentylaminocarbonyl)ethyl]piperazine
1-(3,4,5-Trimethoxycinnamoyl)-4-[1-(cycloheptylaminocarbonyl)ethyl]piperazine.

EXAMPLE 14

1-(3,4,5-Trimethoxycinnamoyl)-4-[1-(isopropylaminocarbonyl)ethyl]piperazine Hydrochloride 3 ml of 15% ethanolic hydrogenchloride is added to a solution of 3.00 g of 1-(3,4,5-trimethoxycinnamoyl)-4-[1-(isopropylaminocarbonyl)ethyl]piperazine prepared as in Example 3 in 5 ml of ethanol, and the solvent is distilled off. Isopropanol is added to the abtained residue and the precipitates are collected by filtration.

Recrystallization of the precipitates from isopropanol gaves 2.00 g of colorless prisms, m.p. 208°–211° C. (decomposition).

Elementary analysis: $C_{22}H_{33}N_3O_5 \cdot HCl$: Calculated: C, 57.95; H, 7.52; N, 9.22. Found: C, 58.26; H, 7.82; N, 8.96.

EXAMPLE 15

1-(3,4,5-Trimethoxycinnamoyl)-4-[1-isopropylaminocarbonyl)ethyl]piperazine Sulfate 0.5 ml of conc. Sulfuric acid is added to a solution of 1.43 g of 1-(3,4,5-trimethoxycinnamoyl)-4-[1-(isopropylaminocarbonyl)ethyl]piperazine prepared as in Example 3 in 25 ml of ethanol.

Thereafter, the procedure according to the Example 14 is repeated and the precipitates are obtained.

Recrystallization of the precipitates from isopropanol gaves 1.00 g of colorless plates, m.p. 229°–232° C. (decomposition).

Elementary analysis: $C_{22}H_{33}N_3O_5 \cdot H_2SO_4$: Calculated: C, 51.05; N, 6.82; N, 8.12. Found: C, 51.09; H, 6.92; N, 8.01.

It is to be understood that the invention is not to be limited to the exact details of operation or exact compounds, compositions, methods, or procedures shown and described, as obvious modifications and equivalents will be apparent to one skilled in the art.

We claim:

1. 1-(3,4,5-Trimethoxycinnamoyl)-4-alkylaminocarbonylethyl piperazines represented by the formula:

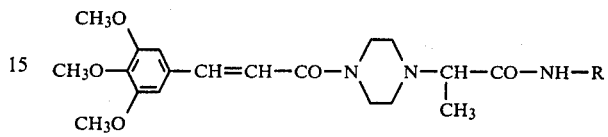

wherein R is a straight- or branched-chain alkyl group having 1 to 6 carbon atoms or a cycloalkyl group having 5 to 7 carbon atoms, and pharmaceutically-acceptable acid addition salts thereof.

2. A pharmaceutical composition, suitable for use in effecting vasodilation, comprising a compound of claim 1, in an amount effective for such purpose, in association with a pharmaceutically-acceptable carrier.

3. A method for the treatment of a subject in need of vasodilation, comprising the step of administering to the said subject a vasodilating amount of a compound of claim 1.

4. A method according to claim 3, wherein the compound of claim 1 is administered in association with a pharmaceutically-acceptable carrier.

5. A compound of claim 1 selected from the group consisting of 1-(3,4,5-trimethoxycinnamoyl)-4-[1-(ethylaminocarbonyl)ethyl]piperazine, 1-(3,4,5-trimethoxycinnamoyl)-4-[1-(propylaminocarbonyl)ethyl]piperazine, 1-(3,4,5-trimethoxycinnamoyl)-4-[1-(isopropylaminocarbonyl)ethyl]piperazine, 1-(3,4,5-trimethoxycinnamoyl)-4-[1-(isobutylaminocarbonyl)ethyl]piperazine, 1-(3,4,5-trimethoxycinnamoyl)-4-[1-(tert-butylaminocarbonyl)ethyl]-piperazine, 1-(3,4,5-trimethoxycinnamoyl)-4-[1-(cyclohexylaminocarbonyl)ethyl]piperazine, 1-(3,4,5-trimethoxycinnamoyl)-4-[1-(methylaminocarbonyl)ethyl]piperazine, 1-(3,4,5-trimethoxycinnamoyl)-4-[1-(butylaminocarbonyl)ethyl]piperazine, 1-(3,4,5-trimethoxycinnamoyl)-4-[1-(sec-butylaminocarbonyl)ethyl]piperazine, 1-(3,4,5-trimethoxycinnamoyl)-4-[1-(pentylaminocarbonyl)ethyl]piperazine, and 1-(3,4,5-trimethoxycinnamoyl)-4-[1-(hexylaminocarbonyl)ethyl]piperazine, preferably, 1-(3,4,5-trimethoxycinnamoyl)-4-[1-(tert-butylaminocarbonyl)ethyl]piperazine, 1-(3,4,5-trimethoxycinnamoyl)-4-[1-(cyclohexylaminocarbonyl)ethyl]piperazine, 1-(3,4,5-trimethoxycinnamoyl)-4-[1-(sec-butylaminocarbonyl)ethyl]piperazine, most preferably, 1-(3,4,5-trimethoxycinnamoyl)-4-[1-isopropylaminocarbonyl)ethyl]piperazine.

* * * * *